United States Patent [19]

Okamoto et al.

[11] Patent Number: 5,032,277

[45] Date of Patent: Jul. 16, 1991

[54] OPTICAL RESOLUTION WITH β-1,4-MANNAN TRIBENZOATE

[75] Inventors: Yoshio Okamoto, Amagasaki; Koichi Hatada, Ikeda; Tohru Shibata, Himeji; Hajime Namikoshi, Himeji; Ichiro Okamoto, Himeji, all of Japan

[73] Assignee: Daicel Chemical Industries, Ltd., Osaka, Japan

[21] Appl. No.: 492,887

[22] Filed: Mar. 9, 1990

Related U.S. Application Data

[60] Division of Ser. No. 266,225, Oct. 28, 1988, Pat. No. 4,931,184, which is a continuation of Ser. No. 716,712, Mar. 27, 1985, abandoned.

[30] Foreign Application Priority Data

Apr. 5, 1984 [JP] Japan .................................. 59-68087

[51] Int. Cl.$^5$ .............................................. B01D 15/08
[52] U.S. Cl. .................................... 210/635; 210/656; 210/198.2; 210/502.1; 502/404
[58] Field of Search ................. 210/198.2, 502.1, 635, 210/656, 500.31, 500.32; 502/404; 55/67, 386

[56] References Cited

U.S. PATENT DOCUMENTS

| | | | |
|---|---|---|---|
| 3,002,823 | 10/1961 | Flodin | 210/635 |
| 4,329,383 | 5/1982 | Joh | 210/500.23 |
| 4,356,236 | 10/1982 | Koshugi | 502/404 |
| 4,426,292 | 1/1984 | Wernick | 210/502.1 |
| 4,452,918 | 6/1984 | Uchida | 210/656 |
| 4,464,165 | 8/1984 | Pollard | 210/635 |
| 4,576,928 | 3/1986 | Tani | 502/404 |
| 4,637,994 | 1/1987 | Tani | 502/401 |
| 4,714,555 | 12/1987 | Shibata | 210/656 |
| 4,786,415 | 11/1988 | Shibata | 210/656 |
| 4,830,752 | 5/1989 | Shibata | 210/635 |
| 4,879,038 | 11/1989 | Namikoshi | 210/635 |
| 4,892,659 | 1/1990 | Shibata | 210/635 |

OTHER PUBLICATIONS

Optical Resolution on Polymer by Okamoto-A Publication Presented to the 49th Annual Meeting of the Chemical Society of Japan, Mar. 10, 1984, (Entire Document and Translation).

*Primary Examiner*—Ernest G. Therkorn
*Attorney, Agent, or Firm*—Flynn, Thiel, Boutell & Tanis

[57] ABSTRACT

A separation agent essentially comprises an aliphatic or aromatic ester of a polysaccharide, except for cellulose acetate and an aromatic ester of cellulose. It is useful for separation of various chemical substances, especially optical resolution of optical isomers.

2 Claims, No Drawings

OPTICAL RESOLUTION WITH β-1,4-MANNAN TRIBENZOATE

This is a division of Ser. No. 07/266 225, filed Oct. 28, 1988, now U.S. Pat. No. 4,931,184 which is a continuation of Ser. No. 06/716 712, filed Mar. 27, 1985, now abandoned.

The invention relates to a separation agent which essentially comprises an aromatic carboxylic acid ester of a polysaccharide. It is useful for separation of various chemical substances, especially optical resolution of optical isomers.

The resolving agent of the present invention can be used for separation of all sorts of chemical substances, particularly for optical resolution of them.

It has been well known that optical isomers of a chemical compound have effects different from each other in vivo generally. Therefore, it is important to obtain optically pure compounds for the purposes of improving medicinal effects per unit dose of them and removing adverse reactions thereof and damages from them in medical, agricultural and biochemical fields. A mixture of optical isomers has been optically resolved by preferential crystallization or diastereomer process. However, varieties of compounds capable of being optically resolved by these processes are limited and these processes require a long time and much labor. Under these circumstances, development of a technique of conducting the optical resolution by an easy chromatographic process has eagerly been demanded.

An object of the present invention is to provide a resolving agent having a chemical structure different from those of known resolving agents.

The above-mentioned object of the present invention is attained by a resolving agent containing an aromatic carboxylic acid ester of a polysaccharide as an effective component.

The resolving agent of the invention exhibits preferably different powers of adsorbing different optical isomers of a given compound.

The term "polysaccharides" herein involves any optically active polysaccharide selected from the group consisting of synthetic, natural and modified natural polysaccharides. Among them, those having highly regular linkages are preferred. Examples of them include β-1,4-glucans (celluloses), α-1,4-glucans (amylose and amylopectin), α-1,6-glucan (dextran), β-1,6-glucan (pustulan), β-1,2-glucan (Crown gall polysaccharide), β-1,4-galactan, β-1,4-mannan, α-1,6-mannan, β-1,2-fructan (inulin), β-2,6-fructan (levan), β-1,4-xylan, β-1,3-xylan, β-1,4-chitosan, β-1,4-N-acetylchitosan (chitin), pullulan, agarose and alginic acid. Still preferred ones are those capable of easily yielding highly pure polysaccharides, such as cellulose, amylose, β-1,4-chitosan, chitin, β-1,4-mannan, β-1,4-xylan, inulin and curdlan.

These polysaccharides have a number-average degree of polymerization (average number of pyranose or furanose rings in the molecule) of at least 5, preferably at least 10. Though there is provided no upper limit of the degree of polymerization, it is preferably 500 or less from the viewpoint of the ease of handling.

The term "aromatic carboxylic acids" herein refers to those having an aromatic ring having 6 to 20 carbon atoms or a heteroaromatic ring having 4 to 20 carbon atoms. Preferred aromatic carboxylic acids are those having carboxyl groups directly bonded with the aromatic or heteroaromatic ring. They may have further a substituent bonded with the ring.

In the polysaccharide, the hydroxyl groups other than those forming the linkage bond with the above-mentioned carboxylic acid may be present in the form of free hydroxyl groups or they may be esterified, etherified or carbamoylated so far as the resolving ability of the resolving agent is not damaged.

The esterification for forming the fatty acid esters of the polysaccharides used in the present invention may be conducted by a known process for the esterification of cellulose or amylose (see, for example, "Dai-Yuki Kagaku" 19, 'Tennen Kobunshi Kagaku I' published by Asakura Book Store, p. 124). For example, generally used esterifying agents are anhydrides and halides of corresponding carboxylic acids, particularly acid chlorides. It is preferred to use a tertiary amine base or Lewis acid as the catalyst. The reaction solvent may be any solvent so far as it does not inhibit the esterification reaction, such as pyridine or quinoline which acts also as the base. Frequently, a catalyst such as 4-(N,N-dimethylamino)pyridine is effective in accelerating the reaction.

Further, a corresponding carboxylic acid combined with a dehydrating agent may also be reacted with the polysaccharide to obtain the ester.

Since most of the polysaccharides used as the starting material have a low reactivity, it is preferably that, they are activated by dissolution/reprecipitation or dissolution/freeze drying treatment or by using a reaction solvent in which the polysaccharides are soluble.

The resolving agent of the present invention is used for the purpose of resolving compounds and optical isomers thereof generally according to a chromatographic method such as gas, liquid or thin layer chromatographic method. Further, the resolving agent may be used in membrane resolution method.

In using the resolving agent of the present invention in the liquid chromatography, there may be employed a method wherein the powdered resolving agent is packed in a column, a method wherein a capillary column is coated with the resolving agent, a method wherein a capillary is made from the resolving agent to use the inner wall thereof and a method wherein the resolving agent is spun and bundled up to form a column. Among them, the method wherein the powdered resolving agent is employed is most general.

The separation agent of the invention is preferably used in the form of powder. It is obtained by crushing the agent or forming it into spherical beads. The particle size which varies depending on the size of a column or plate used is 1 μm to 10 mm, preferably 1 to 300 μm. The particles are preferably porous.

It is preferred to support the resolving agent on a carrier so as to improve the resistance thereof to pressure or to prevent swelling or shrinkage thereof due to solvent exchange and from the viewpoint of the number of theoretical plates. The suitable size of the carrier which varies depending on the size of the column or plate used is generally 1 μm to 10 mm, preferably 1 to 300 μm. The carrier is preferably porous and has an average pore diameter of 10 Å to 100 μm, preferably 50 to 50,000 Å. The amount of the resolving agent to be supported is 1 to 100 wt. %, preferably 5 to 50 wt. %, based on the carrier.

The resolving agent may be supported on the carrier by either chemical or physical means. The physical means include one wherein the resolving agent is dissolved in a suitable solvent, the resulting solution is mixed with a carrier homogeneously and the solvent is distilled off by means of a gaseous stream under reduced pressure or heating and one wherein the resolving agent is dissolved in a suitable solvent, the resulting solution is mixed homogeneously with a carrier and the mixture is dispersed in a liquid incompatible with said solvent by stirring to diffuse the solvent. The resolving agent thus supported on the carrier may be crystallized, if necessary, by heat treatment or the like. Further, the state of the supported resolving agent and accordingly its resolving power can be modified by adding a small amount of a solvent thereto to temporarily swell or dissolve it and then distilling the solvent off.

Both porous organic and inorganic carriers may be used, though the latter is preferred. The suitable porous organic carriers are those comprising a high molecular substance such as polystyrene, polyacrylamide or polyacrylate. The suitable porous inorganic carriers are synthetic or natural products such as silica, alumina, magnesia, titanium oxide, glass, silicate or kaolin. They may be surface-treated so as to improve their affinity for the resolving agent. The surface treatment may be effected with an organosilane compound or by plasma polymerization.

In using the resolving agent of the present invention in the resolution of compounds or optical isomers, the resolving characteristics thereof may vary sometimes depending on physical properties thereof such as molecular weight, crystallinity and orientation, even though they are chemically similar. Therefore, the resolving characteristics of the resolving agent may be altered according to the use thereof by suitably selecting the solvent used in that step or by physical treatments such as heat treatment, etching or swelling with the liquid after said step in any of the above-mentioned processes.

In liquid or thin layer chromatography, any developer may be used except those in which the resolving agent is soluble or which are reactive with the resolving agent. In case the resolving agent has been bound to the carrier by the chemical process or it has been insolubilized by crosslinking, any solvent other than a reactive liquid may be used. As a matter of course, it is preferred to select the developer after examination of various developers, since the resolving characteristics of chemical substances or optical isomers vary depending on the developer used.

In the thin layer chromatography, a layer having a thickness of 0.1 to 100 mm and comprising the resolving agent in the form of particles of about 0.1 μm to 0.1 mm and, if necessary, a small amount of a binder is formed on a supporting plate.

In the membrane resolution process, the resolving agent is used in the form of a hollow filament or film.

The resolving agent of the present invention containing the aromatic ester of the polysaccharide as the effective component is effective for the resolution of various compounds. Particularly, it is quite effective for the resolution of optical isomers which are quite difficult to resolve. Either one of the optical isomers to be resolved is selectively adsorbed on the resolving agent.

The separation agent according to the invention is useful to the optical resolution as above shown. In addition, it serves for separation of geometrical isomers and polymers having different molecular weight ranges from each other. They have not easily been separated in the state of prior arts.

The following examples will further illustrate the present invention, which by no means limit the invention. In the examples, the terms are defined as follows:

$$\text{capacity ratio } (k') = \frac{\left(\begin{array}{c}\text{retention volume}\\\text{of enantiomer}\end{array}\right) - (\text{void volume})}{(\text{void volume})}$$

$$\text{separation factor } (\alpha) = \frac{\left(\begin{array}{c}\text{capacity ratio of enantiomer}\\\text{adsorbed more strongly}\end{array}\right)}{\left(\begin{array}{c}\text{capacity ratio of enantiomer}\\\text{adsorbed less strongly}\end{array}\right)}$$

$$\text{rate of separation } (Rs) = \frac{2 \times \left(\begin{array}{c}\text{distance between a peak}\\\text{of more strongly adsorbed}\\\text{enantiomer and that of}\\\text{less strongly adsorbed enantiomer}\end{array}\right)}{(\text{total band width of both peaks})}$$

SYNTHESIS EXAMPLE 1

10 g of silica beads (LiChrospher SI 1000; a product of Merck & Co.) was placed in a 200 ml round-bottom flask with a side arm. After vacuum-drying in an oil bath at 120° C. for 3 h, $N_2$ was introduced therein. 100 ml of toluene which had been preliminarily distilled in the presence of $CaH_2$ was added to the silica beads. 3 ml of diphenyldimethoxysilane (KBM 202; a product of Shin'etsu Kagaku Co., Ltd.) was added to the mixture and they were stirred together and then reacted at 120° C. for 1 h. After distilling off 3 to 5 ml of toluene, the reaction was carried out at 120° C. for 2 h. The mixture was filtered through a glass filter, washed with 50 ml of toluene three times and then with 50 ml of methanol three times and dried in vacuum at 40° C. for 1 h.

About 10 g of the silica beads were placed in the 200 ml round-bottom flask with a side arm. After vacuum drying at 100° C. for 3 h, the pressure was returned to atmospheric pressure and the mixture was cooled to room temperature. Then $N_2$ was introduced therein. 100 ml of distilled toluene was added to the dried silica beads. 1 ml of N,O-bis(trimethylsilyl)acetamide (a trimethylsilylating agent) was added thereto and the mixture was stirred to effect the reaction at 115° C. for 3 h. The reaction mixture was collected with a glass filter, washed with toluene and dried under vacuum for about 4 h.

SYNTHESIS EXAMPLE 2

10 g of silica beads (LiChrospher SI 1000; a product of Merck & Co.) was placed in a 200 ml round-bottom flask with a side arm. After vacuum-drying in an oil bath at 120° C. for 3 h, $N_2$ was introduced therein. 100 ml of toluene which had been preliminarily distilled in the presence of $CaH_2$ was added to the silica beads. 3 ml of diphenyldimethoxysilane (KBM 202; a product of Shin'etsu Kagaku Co., Ltd.) was added to the mixture and they were stirred together and then reacted at 120° C. for 1 h. After distilling off 3 to 5 ml of toluene, the reaction was carried out at 120° C. for 2 h. The mixture was filtered through a glass filter, washed with 50 ml of toluene three times and then with 50 ml of methanol three times and dried in vacuum at 40° C. for 1 h.

About 10 g of the silica beads were placed in the 200 ml round-bottom flask with a side arm. After vacuum drying at 100° C. for 3 h, the pressure was returned to the atmospheric pressure and the mixture was cooled to room temperature. Then $N_2$ was introduced therein. 100 ml of distilled toluene was added to the dried silica beads. 1 ml of N,O-bis(trimethylsilyl)acetamide (a trimethylsilylating agent) was added thereto and the mixture was stirred to effect the reaction at 115° C. for 3 h. The reaction mixture was filtered through a glass filter, washed with toluene and dried under vacuum for about 4 h.

SYNTHESIS EXAMPLE 3

Synthesis of β-1,4-Mannan Tribenzoate

Albumens of seeds of ivory palm were treated by a process disclosed in literature [see G. O. Aspinall et al., "J. Chem. Soc.", 3184 (1953)] to obtain mannan B from a high molecular weight fraction. 1.5 g of powder of mannan B was mixed with 70 ml of dehydrated pyridine, 7.7 ml of dehydrated triethylamine and 50 mg of 4-dimethylaminopyridine. 10.7 ml of benzoyl chloride was added thereto under stirring. The reaction was carried out at 100° C. for 5 h. After cooling, the product was added to 400 ml of ethanol under stirring to form a precipitate, which was filtered through a glass filter and washed thoroughly with ethanol. After vacuum drying, the product was dissolved in 30 ml of methylene chloride and the insoluble matter was removed. The product was reprecipitated from 400 ml of ethanol. The precipitate was collected by filtration, washed with ethanol, dehydrated and dried.

The product was dissolved in methylene chloride. The solution was applied to a common salt tablet and dried. The infrared absorption spectrum of the product had the following characteristic absorption bands:

- 3070 cm$^{-1}$: stretching vibration of aromatic C—H,
- 1730 cm$^{-1}$: stretching vibration of C=O of carboxylic acid ester,
- 1605, 1495, 1455 cm$^{-1}$: skeletal vibration due to stretching of carbon and carbon in the benzene ring,
- 1270 cm$^{-1}$: stretching vibration of C—O of ester,
- 1030 to 1200 cm$^{-1}$: stretching vibration of C—O—C of mannan, and
- 690 to 900 cm$^{-1}$: out-of-plane deformation vibration of benzene ring.

Substantially no absorption at around 3450 cm$^{-1}$ due to OH of mannan was observed. This fact suggested that the product substantially comprised a trisubstituted compound. In the proton NMR spectrum determined in CDCl$_3$, the characteristic absorptions were as follows:

- 6.8 to 8.4 ppm: proton of benzene ring,
- 2.8 to 6.0 ppm: protons of mannan ring and methylene in position 6.

The ratio of these absorption intensities was 15:7.

SYNTHESIS EXAMPLE 4

Synthesis of Tribenzoyl-β-1,4-Chitosan 10 g of purified chitosan was dissolved in 1000 ml of water containing 40 ml of conc. hydrochloric acid. The solution was kept at 73° C. for 5 h. The solution was concentrated by means of a rotary evaporator and then neutralized with 27 ml of aqueous ammonia (28%) to precipitate chitosan. The precipitate was collected by filtration, washed with water, ethanol and then ether each twice and dried in vacuo. Yield: 9.71 g.

1.0 g of obtained chitosan was dissolved in 30 ml of water containing 0.5 ml of conc. hydrochloric acid. The solution was freeze-dried. 30 ml of pyridine, 0.05 g of 4-dimethylaminopyridine, 8 ml of triethylamine and 10 ml of benzoyl chloride were added to the residue and the mixture was kept at 100° to 105° C. under stirring for 7 h. The resulting suspension was added to ethanol to form a precipitate, which was filtered, washed with ether and then with dichloromethane and dried in vacuo. Yield: 3.0 g. In the I.R. spectrum, two carbonyl stretching vibrations were observed at 1720 and 1660 cm$^{-1}$. This fact suggested that the product was tribenzoylchitosan.

EXAMPLE 1

1.2 g of β-1,4-mannan tribenzoate obtained in Synthesis Example 3 was dissolved in a mixture of 12.5 ml of dichloromethane and 3.5 ml of acetone. 6.4 g of the silica gel particles obtained in Synthesis Example 2 were impregnated with the solution. The solvent was distilled off under reduced pressure to obtain a powdery, supported material.

EXAMPLE 2

1.2 g of tribenzoylchitosan obtained in Synthesis Example 4 was dissolved in a mixture of 5 ml of dichloromethane and 4.5 ml of dichloroacetic acid. The solution was filtered. 3.2 g of the silica gel obtained in Synthesis Example 1 was impregnated with 7.5 ml of the solution. The vessel was heated with hot water under reduced pressure realized by means of a vacuum pump to remove the solvent. A powdery, supported material was thus obtained.

APPLICATION EXAMPLE 1

The silica beads carrying mannan tribenzoate obtained in Example 1 were packed in a stainless steel column having a length of 25 cm and an inner diameter of 0.46 cm by slurry process. The high performance liquid chromatograph used was TRIROTAR-SR (a product of Japan Spectroscopic Co., Ltd.) and the detector was UVIDEC-V. The results of the resolution of 2-phenylcyclohexanone are shown in Table 1.

TABLE 1

| Racemates | capacity ratio | | Resolution factor | Rate of separation | Flow rate |
|---|---|---|---|---|---|
| | $k_1'$ | $k_2'$ | α | Rs | ml/min |
| 2-phenylcyclohexanone | 3.80 | 4.02 | 1.06 | 0.5 | 0.5 |

Solvent: hexane/2-propanol (9:1)

APPLICATION EXAMPLE 2

The silica beads carrying tribenzoylchitosan obtained in Example 2 were suspended in methanol. The suspension was packed in a stainless steel column having a length of 25 cm and an inner diameter of 0.46 cm by slurry process. The high performance liquid chromatograph used was TRIROTAR-SR (a product of Japan Spectroscopic Co., Ltd.) and the polarimeter detector was DIP-181 (a product of Japan Spectroscopic Co., Ltd.). The results of the resolution of racemic compounds are shown in Table 2.

In the determination effected by using the polarimeter as the detector of the high performance chromatograph, the terms were defined as follows:

$$t' = \frac{\begin{pmatrix} \text{time required for attaining the} \\ \text{top of the peak of enantiomer} \\ \text{with the polarimeter detector} \end{pmatrix} - \begin{pmatrix} \text{dead} \\ \text{time} \end{pmatrix}}{\text{(dead time)}}$$

$$\beta = \frac{(t' \text{ of enantiomer adsorbed more strongly})}{(t' \text{ of enantiomer adsorbed less strongly})}$$

TABLE 2

| racemates | $l_1'$ | $l_2'$ | $\beta$ | Flow rate (ml/min) |
|---|---|---|---|---|
| [diphenyl ether structure] | 1.56 | 1.88 | 1.21 | 1.0 |

Solvent: hexane/2-propanol (9:1)

SYNTHESIS EXAMPLE 5

Synthesis of β-1,4-Xylan Benzoate 5.0 g of xylan (a product of Tokyo Kasei Co.) was dispersed in 10 ml of water. A 30% aqueous sodium hydroxide solution was added to the dispersion under cooling with ice until xylan had been dissolved to form a transparent solution. The solution was added to 150 ml of methanol containing 3 ml of acetic acid to form a precipitate, which was filtered and washed with methanol. About a half of the precipitate was suspended in a mixture of 40 ml of benzene and 40 ml of pyridine. Benzene was distilled off from the reaction system through a 20 cm column. 20 ml of benzoyl chloride was added thereto and the mixture was kept at 90° C. for 10 h. The mixture was cooled and then added to 500 ml of ethanol to form a precipitate, which was filtered, washed and dried. The product was dissolved in dichloromethane. An insoluble matter was removed by filtration. Dichloromethane was distilled off under reduced pressure to obtain xylan dibenzoate. In the I.R. absorption spectrum of this produce, the absorption due to the stretching vibration of OH was weak.

EXAMPLE 3

1.2 g of β-1,4-xylan dibenzoate obtained in Synthesis Example 5 was dissolved in 7.5 ml of dichloromethane. The solution was filtered through a glass filter (G2) and the filtrate was mixed with 3.4 g of the silica beads obtained in Synthesis Example 2. The solvent was distilled off under reduced pressure to obtain a powdery, supported material.

APPLICATION EXAMPLE 3

The results of the optical resolution of racemic compounds conducted with the supported material obtained in Example 3 under the same conditions as in Application Example 1 are shown in Table 3.

TABLE 3

| racemates | capacity ratio $k_1'$ | capacity ratio $k_2'$ | Resolution factor $\alpha$ |
|---|---|---|---|
| [diphenyl ether structure] | 1.75(+) | 2.04(−) | 1.17 |
| [phenyl cyclohexyl ketone structure] | 4.91(−) | 5.74(+) | 1.17 |

Eluent: hexane/2-propanol (9:1)
Flow rate: 0.5 ml/min

SYNTHESIS EXAMPLE 6

20 g of purified chitosan (a product of Kyowa Kasei Co.) was dispersed in 1 l of water. 40 ml of conc. hydrochloric acid was added slowly to the dispersion to dissolve chitosan. The resulting solution was kept at 80° C. for 5 h and then cooled. The solids suspended therein was filtered out. The filtrate was concentrated to a volume of 200 ml by means of a rotary evaporator. The liquid was made alkaline with excess aqueous ammonia. Chitosan having a reduced molecular weight was thus precipitated. After collection, the product was washed with water and then ethanol and dried. 1.0 g of the resulting chitosan was dispersed in 10 ml of water. Hydrochloric acid was added in portions to the dispersion until a solution was obtained. The solution was added to 60 ml of methanol containing 3 ml of aqueous ammonia (28%) to precipitate chitosan. After filtration, the product was washed with methanol twice and then with ether twice. Chitosan containing the solvent was added to 60 ml of pyridine. A part (about 30 ml) of pyridine was distilled off. 10 ml of benzoyl chloride was added dropwise to the obtained chitosan-containing pyridine and the mixture was kept at 80° to 90° C. for 8 h. A suspension thus formed was added to cooled methanol to form a precipitate. After filtration, the product was washed with methanol, acetone and dichloromethane and then dried.

EXAMPLE 4

1.05 g of tribenzoylchitosan obtained in Synthesis Example 6 was dissolved in a mixture of 4.0 ml of dichloromethane, 3.0 ml of trifluoroacetic acid and 0.5 ml of benzoyl chloride. The solution was mixed with 3.2 g of the silica beads obtained in Synthesis Example 2. The solvent was distilled off under reduced pressure to obtain a powdery, supported material.

APPLICATION EXAMPLE 4

The optical resolution of racemic compounds was conducted with the supported material obtained in Example 4 in the same manner as in Application Example 1. The results are shown in Table 4. It was noted that Trödger's bases which could not be resolved with cellulose tribenzoate were resolved.

TABLE 4

| racemates | capacity ratio | | Resolution factor |
| --- | --- | --- | --- |
| | $k_1'$ | $k_2'$ | $\alpha$ |
| 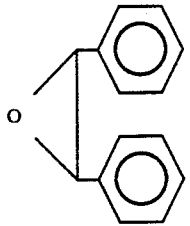 | 1.71(−) | 1.85(+) | 1.08 |
| 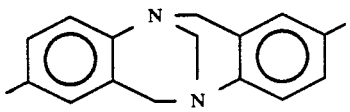 | 1.31(+) | 1.61(−) | 1.23 |
| 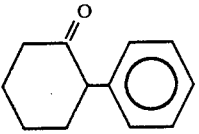 | 3.93(−) | 4.28(+) | 1.09 |
| 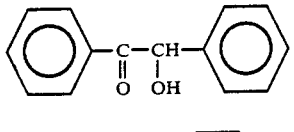 | 6.64 | 7.28 | 1.10 |
| 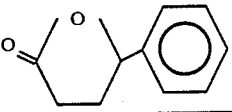 | 14.6(+) | 15.9(−) | 1.09 |

Eluent: hexane/2-propanol (9:1)
Flow rate: 0.5 ml/min.

SYNTHESIS EXAMPLE 7

Synthesis of Mannan A Tribenzoate

Albumens of seeds of ivory palm were treated by a process disclosed in literature [see G. O. Aspinall et al., "J. Chem. Soc.", 3184 (1953)] to obtain mannan A from a low molecular weight fraction.

1.5 g of mannan A was dispersed in a solution comprising 70 ml of pyridine, 7.7 ml of triethylamine and 50 mg of 4-dimethylaminopyridine. 10.7 ml of benzoyl chloride was added to the dispersion and the reaction was carried out at 100° C. for 5 h. After cooling, the reaction mixture was added to ethanol to form a precipitate, which was washed thoroughly with ethanol and dried. The dried sample was dissolved in methylene chloride. The solution was filtered through a glass filter (G3). The filtrate was added to ethanol to form a precipitate, which was washed thoroughly with ethanol and dried.

EXAMPLE 5

1.2 g of mannan A tribenzoate obtained in Synthesis Example 7 was dissolved in 7.5 ml of dichloromethane. The solution was filtered through a glass filter (G-2). The filtrate was mixed thoroughly with 3.4 g of the silica beads obtained in Synthesis Example 2. The solvent was distilled off under reduced pressure to obtain a powdery, supported material.

APPLICATION EXAMPLE 5

The optical resolution of racemic compounds of γ-phenyl-γ-butyrolactone was conducted with the supported material obtained in Example 5 in the same manner as in Application Example 1. The resolution factor (α) was 1.22 [(+) compound being eluted first]. The eluent was hexane/2-propanol (9:1). The flow rate was 0.5 ml/min.

SYNTHESIS EXAMPLE 8

Synthesis of Dextran Tribenzoate 3.0 g of dextran (a product of Nakai Kagaki Yakuhin Co. having a molecular weight of 50,000 to 70,000) was dissolved in 10 ml of water. Pyridine was added to the solution to precipitate dextran. Pyridine was removed by decantation. Additional 20 ml of pyridine was added and then removed by the decantation. The addition and decantation of pyridine were repeated three times. Then, 30 ml of pyridine and 20 ml of benzoyl chloride were added thereto and the mixture was kept at 70° C. for 10 h. After cooling, pyridinium chloride and unreacted dextran were removed by means of a glass filter (G-2). The filtrate was concentrated under reduced pressure. Methanol was added thereto to precipitate dextran tribenzoate, which was filtered, washed with methanol and dried. In the I.R. absorption spectrum of the product, the absorption due to stretching vibration of OH was weak. This fact suggested that the product was a trisubstituted compound.

EXAMPLE 6

1.2 g of dextran tribenzoate obtained in Synthesis Example 8 was dissolved in 7.5 ml of dichloromethane.

The solution was mixed thoroughly with 3.6 g of the silica gel obtained in Synthesis Example 2. The solvent was distilled off under reduced pressure to obtain a powdery, supported material.

APPLICATION EXAMPLE 6

The optical resolution of trans-stilbene oxide was conducted with the supported material obtained in Example 6 in the same manner as in Application Example 1. The resolution factor was 1.18. The enantiomer having (−) optical rotation was eluted first. The eluent was hexane/2-propanol (9:1). The flow rate was 0.5 ml/min.

The embodiments of the invention in which an exclusive property or privilege is claimed are defined as follows:

1. A method for chromatographically separating optical isomers from a mixture thereof, which comprises the step of contacting said mixture, under conditions effective for chromatographic separation, with β-1,4-mannan tribenzoate having an esterification ratio of 85 percent or more as the chromatographic separation agent.

2. A method as claimed in claim 1, in which the contacting step comprises conducting said mixture through a chromatographic column or layer comprising said β-1,4-mannan tribenzoate to effect separation and resolution of the components of said mixture.

* * * * *